(12) United States Patent
Wiemker et al.

(10) Patent No.: US 9,706,968 B2
(45) Date of Patent: Jul. 18, 2017

(54) DETERMINING A RESIDUAL MODE IMAGE FROM A DUAL ENERGY IMAGE

(71) Applicants: KONINKLIJKE PHILIPS N.V., Eindhoven (NL); PHILIPS DEUTSCHLAND GMBH, Hamburg (DE)

(72) Inventors: Rafael Wiemker, Kisdorf (DE); Thomas Buelow, Grosshansdorf (DE); Andre Goossen, Radbruch (DE); Klaus Erhard, Hamburg (DE); Martin Bergtholdt, Hamburg (DE); Harald Sepp Heese, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 16 days.

(21) Appl. No.: 14/774,205

(22) PCT Filed: Mar. 14, 2014

(86) PCT No.: PCT/IB2014/059770
§ 371 (c)(1),
(2) Date: Sep. 10, 2015

(87) PCT Pub. No.: WO2014/141163
PCT Pub. Date: Sep. 18, 2014

(65) Prior Publication Data
US 2016/0038112 A1 Feb. 11, 2016

Related U.S. Application Data

(60) Provisional application No. 61/787,489, filed on Mar. 15, 2013.

(51) Int. Cl.
*G06T 5/50* (2006.01)
*A61B 6/00* (2006.01)
(Continued)

(52) U.S. Cl.
CPC ............. *A61B 6/482* (2013.01); *A61B 6/463* (2013.01); *A61B 6/502* (2013.01); *A61B 6/5235* (2013.01);
(Continued)

(58) Field of Classification Search
None
See application file for complete search history.

(56) References Cited

U.S. PATENT DOCUMENTS 4,789,930 A   12/1988  Sones et al.
6,240,217 B1   5/2001  Ercan et al.
(Continued)

FOREIGN PATENT DOCUMENTS

GB    2464574 A    4/2010

OTHER PUBLICATIONS

G.K. Matsopoulos, "Medical imaging correction: A comparative study of five contrast and brightness matching methods", Computer Methods and Programs in Biomedicine, vol. 106, No. 3, Jun. 1, 2012, pp. 308-327, XP055129300, ISSN: 0169-2607.
(Continued)

*Primary Examiner* — Tsung-Yin Tsai

(57) ABSTRACT

A digital image (40) comprises pixels with intensities relating to different energy levels. A method for processing the digital image (40) comprises the steps of: receiving first image data (42a) and second image data (42b) of the digital image (40), the first image data (42a) encoding a first energy level and the second image data (42b) encoding a second energy level; determining a regression model (44) from the first image data (42a) and the second image data (42b), the regression model (44) establishing a correlation between intensities of pixels of the first image data (42a) with intensities of pixels of the second image data (42b); and calculating residual mode image data (46) from the first
(Continued)

image data (42a) and the second image data (42b), such that a pixel of the residual mode image data (46) has an intensity based on the difference of an intensity of the second image data (42b) at the pixel and a correlated intensity of the pixel of the first image data (42a), the correlated intensity determinate by applying the regression model to the intensity of pixel of the first image data (42a).

14 Claims, 4 Drawing Sheets

(51) Int. Cl.
*G06T 7/00* (2017.01)
*G06T 11/60* (2006.01)
*G06T 7/136* (2017.01)

(52) U.S. Cl.
CPC .............. *A61B 6/54* (2013.01); *G06T 5/50* (2013.01); *G06T 7/0012* (2013.01); *G06T 7/136* (2017.01); *G06T 11/60* (2013.01); *A61B 6/467* (2013.01); *G06T 2207/10116* (2013.01); *G06T 2207/20104* (2013.01); *G06T 2207/30068* (2013.01); *G06T 2210/41* (2013.01); *G06T 2211/408* (2013.01)

(56) References Cited

U.S. PATENT DOCUMENTS

| | | | |
|---|---|---|---|
| 7,599,465 B2 | 10/2009 | Walter et al. | |
| 7,953,249 B2 * | 5/2011 | Mertens | G01J 3/46 382/112 |
| 8,165,379 B2 | 4/2012 | Puong et al. | |
| 9,477,875 B2 * | 10/2016 | Ohya | G06K 9/00147 |
| 2002/0186875 A1 * | 12/2002 | Burmer | G06K 9/66 382/133 |
| 2008/0292194 A1 * | 11/2008 | Schmidt | G06T 7/0012 382/217 |
| 2012/0014584 A1 | 1/2012 | Han et al. | |
| 2012/0081386 A1 | 4/2012 | Wiemker et al. | |
| 2012/0134603 A1 * | 5/2012 | Pang | G06T 5/009 382/294 |
| 2012/0257808 A1 | 10/2012 | Spitzer et al. | |
| 2013/0034272 A1 * | 2/2013 | Thomas | G06T 7/0016 382/107 |
| 2013/0236124 A1 * | 9/2013 | Wiemker | G06T 11/60 382/294 |

OTHER PUBLICATIONS

Thorsten M. Buzug et al, "Using an entropy similarity measure to enhance the quality of DSA Images with an Algorithm Based on Template Matching", Visualization in Biomedical Computing: 4th International Conference, VBC'96, Hamburg, Germany, Sep. 22-25, 1996, Springer, DE, pp. 235-240, XP019193767, ISBN: 978-3-540-61649-8.

Angelo Taibi, "Generalized subtraction methods in a digital mammography", European Journal of Radiology, Elsevier Science, NL., vol. 72, No. 3, Dec. 1, 2009, pp. 447-453, XP026777190, ISSN: 0720-048X.

Ohki M. Masafumi et al, "A contrast-correction method for digital subtraction radiography", Journal of Periodontal Research, vol. 23, No. 4, Jul. 1, 1988, pp. 277-280, XP055129330, ISSN: 0022-3484.

* cited by examiner

DETERMINING A RESIDUAL MODE IMAGE FROM A DUAL ENERGY IMAGE

CROSS-REFERENCE TO PRIOR APPLICATIONS

This application is the U.S. National Phase application under 35 U.S.C. §371 of International Application No. PCT/IB2014/, filed on Mar. 14, 2014, which claims the benefit of U.S. Provisional Patent Application No. 61/787,489, filed on Mar. 15, 2013. These applications are hereby incorporated by reference herein.

FIELD OF THE INVENTION

The invention relates to a method, a computer program, a computer-readable medium and a controller for processing a digital image comprising pixels with intensities relating to different energy levels of record. Additionally, the invention relates to an X-ray imaging system.

BACKGROUND OF THE INVENTION

In medical imaging, for example in X-ray mammography, transmission images of a region of interest of a patient, such as a breast, may be recorded by detecting X-rays that fall onto a sensor or detector after having passed the region of interest. After that these images may be displayed and a physician or similarly skilled person may decide, whether there are malignant or benign changes in the region of interest.

An X-ray imaging system may comprise an energy discriminating detector, i.e. a detector that is adapted for differentiating between X-rays of different energy and of recording images at different energy levels. For example, a dual energy detector may produce two energy images of exactly the same geometry and anatomical area.

U.S. Pat. No. 8,165,379 B2 shows a mammography system that is adapted to record low energy and high energy images.

Two complementing energy images may show information which may help to discriminate whether visible masses are likely malignant or benign. However, the way to compute malignancy features from the dual energy images is not yet clear.

SUMMARY OF THE INVENTION

There may be a need to support a physician by evaluating images of a region of interest recorded at different energy levels.

This need may be met by the subject-matter of the independent claims. Further exemplary embodiments are evident from the dependent claims and the following description.

An aspect of the invention relates to a method for processing a digital image, which comprises pixels with intensities relating to different energy levels. I.e. each pixel of the image may be associated with at least two intensities, which have been recorded at different energy levels. The digital image may be a digital X-ray image and the energies may relate to different X-ray energies during the recording of the digital X-ray image.

The method comprises the steps of: receiving first image data and second image data of the digital image, the first image data encoding a first energy level and the second image data encoding a second energy level; determining a regression model from the first image data and the second image data, the regression model establishing a correlation between intensities of pixels of the first image data with intensities of pixels of the second image data; and calculating residual mode image data from the first image data and the second image data, such that a pixel of the residual mode image data has an intensity based on the difference of an intensity of the second image data at the pixel and a correlated intensity of the pixel of the first image data, the correlated intensity determinate by applying the regression model to the intensity of pixel of the first image data.

The basic idea of the invention may be seen that two energy images, i.e. a first energy image and a second energy image (represented by the first (energy) image data and the second (energy) image data) are recorded and evaluated such that new information is extracted from the two energy images that may not be directly seen by simply comparing the two energy images. This new information may be visualized with the residual mode image data.

For example, for extracting the new information, a correlation between the two energy images may be analyzed, and a regression model may be established based on the correlation. The regression model may be used for predicting an intensity of each pixel in the second energy image from the intensity of the same pixel in the first energy image.

For visualizing the new information, new images (represented by corresponding image data) may be computed with the aid of the regression model. For example, the residual mode image (represented by residual mode image data) may display information in the second image that could not be predicted from the first image, i.e. new information. Furthermore, a dominant mode image (represented by dominant mode image data) may display highly correlated components in the two energy images.

Summarized, with the method as described as above and in the following, a computation of malignancy features from dual energy images may be improved. For this purpose, with the residual mode image it may be established which parts of a second energy image significantly add information to a first energy image.

Further aspects of the invention relate to a computer program, a computer-readable medium and a controller, which are adapted to execute the steps of the method as described as above and below. A computer-readable medium may be a floppy disk, a hard disk, an USB (Universal Serial Bus) storage device, a RAM (Random Access Memory), a ROM (Read Only Memory), an EPROM (Erasable Programmable Read Only Memory) or a FLASH memory. A controller may comprise a processor for executing the computer program, which may be stored in a memory of the controller.

Another aspect of the invention relates to an X-ray imaging system, which comprises a detector arrangement for recording first image data with X-rays of a first energy level and for recording second image data with X-rays of a second energy level, a controller, which is adapted for generating residual mode image data from the first image data and the second image data, and a display device for displaying the residual mode image data. For example, the X-ray imaging system may be a mammography station.

However, it is also possible that the image data is recorded at a first place and processed at a second place, for example at a workstation remotely connected to an X-ray device.

It has to be understood that features of the method as described in the above and in the following may be features of the X-ray imaging system as described in the above and in the following.

If technically possible but not explicitly mentioned, also combinations of embodiments of the invention described in the above and in the following, and in particular combinations of depended claims may be embodiments of the method and the system.

These and other aspects of the invention will be apparent from and elucidated with reference to the embodiments described hereinafter.

DETAILED DESCRIPTION OF EMBODIMENTS

Figure 1:
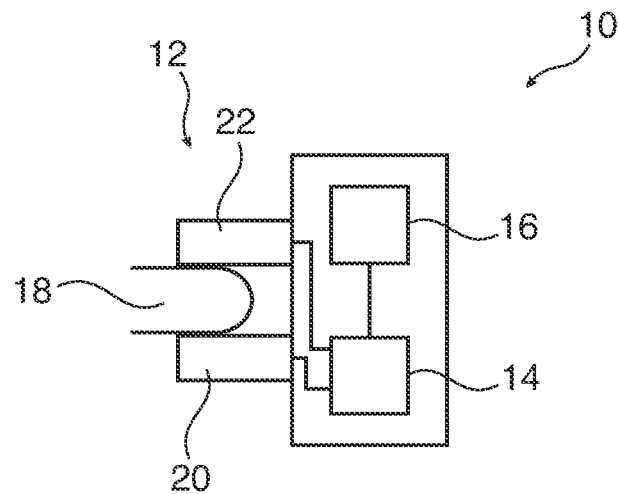
FIG. 1 schematically shows an X-ray imaging system according to an embodiment of the invention.

FIG. 1 shows an X-ray imaging system 10 that comprises a detector arrangement 12, a controller 14 and a display device 16.

The detector arrangement 12, which may be controlled by the controller 14, is adapted for recording digital images at two different energy levels of an object of interest 18, such as a breast. For example, the detector arrangement 12 may comprise an energy discriminating detector 20 or an X-ray source 22 that is adapted for generating X-ray radiation at different energy levels at different times.

Figure 2:
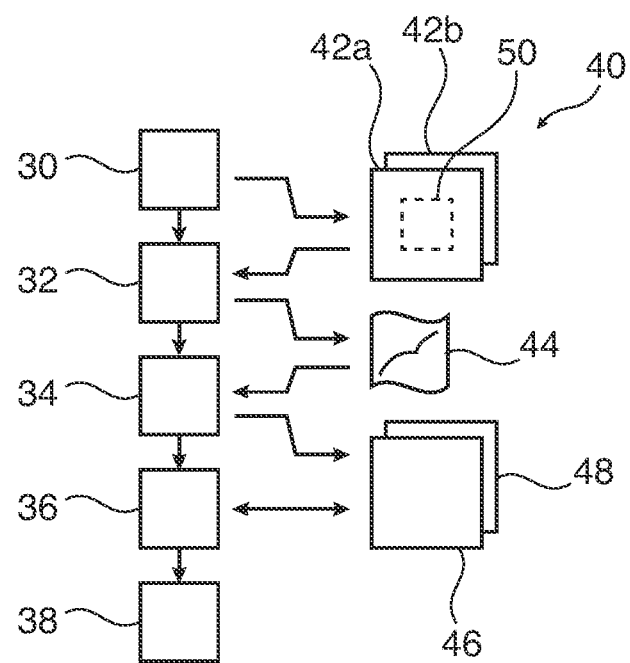
FIG. 2 shows a flow diagram for a method for processing image data according to an embodiment of the invention.

FIG. 2 shows a flow diagram for a method for processing a digital image 40 that may be recorded by the detector arrangement 12. The method may be executed by the controller 14, which, for example, may comprise a processor running a corresponding computer program.

In step 30, the digital image 40 is recorded and received in the controller 14. As already noted, the controller 14 may control the detector arrangement 12 in such a way that digital image data 42a, 42b is recorded at different energy levels, for example with an energy discriminating detector 20.

It has to be noted that the image 40 and its parts 42a, 42b may be recorded simultaneously or during a short time period. In such a way, the image 40 may show the same geometry of the region of interest 18 and/or the same anatomical area 18.

According to an embodiment of the invention, the method comprises the step of: recording the first image data 42a and the second image data 42b with an X-ray detector arrangement 12 adapted for acquiring X-rays at different X-ray energy levels.

After that, the digital image 40 is received in the controller 14. Each of the first and second image data 42a, 42b (or energy image data 42a, 42b) comprises pixels associated with intensities relating to the intensity of the respective energy level at the respective pixel. The first and second image data 42a, 42b may have the same size in pixels (as representing the same field of view on the region of interest). It has to be noted that the digital image 40 may comprise more than two sets of image data 42a, 42b, associated with more than two energy levels.

According to an embodiment of the invention, the method comprises the step of: receiving first image data 42a and second image data 42b of the digital image 40, the first image data 42a encoding a first energy level and the second image data 42b encoding a second energy level.

In step 32, a regression model is determined from the first and second image data 42a, 42b.

Figure 4:
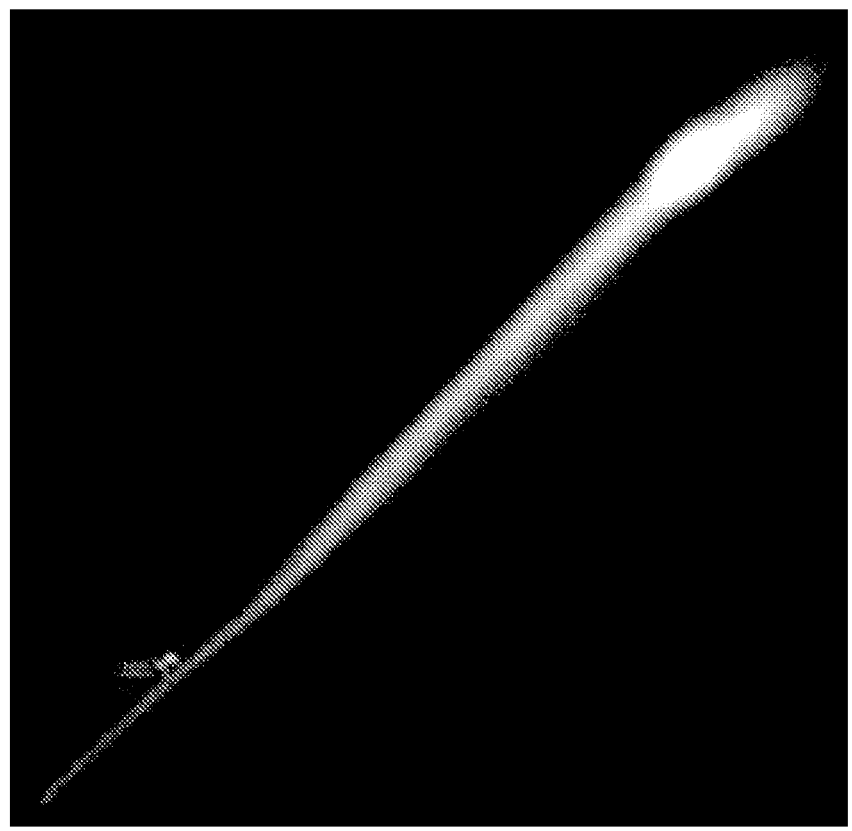
FIG. 4 shows an example for a correlation of energy intensities of two images.

FIG. 4 shows an example of a pixel-wise scatter plot of the intensities of two sets of energy image data 42a, 42b, which show a high but non-linear correlation. This correlation between the two sets of energy image data is analyzed, to generate a regression model 44.

For example, the regression model 44 is a mapping that maps an intensity of a pixel of the first image data 42a to an intensity of the second image data 42b. In other words, with the regression model, an intensity of each pixel in the second image data 42b may be predicted from the corresponding intensity in the first image data 42a.

According to an embodiment of the invention, the method comprises the step of: determining a regression model 44 from the first image data 42a and the second image data 42b, the regression model 44 establishing a correlation between intensities of pixels of the first image data 42a with intensities of pixels of the second image data 42b.

The regression model 44 may be derived either for the whole image area (i.e. all pixels of the image data 42a, 42b) or only for a selected region 50, which may be selected by a user, as will be explained below.

According to an embodiment of the invention, the regression model 44 is determined from pixels of only a selected region 50.

As may be seen from the FIG. 4, the correlation between the two sets of image data 42a, 42b may be non-linear. Therefore, it is possible that a non-linear regression model 44 is established, for example a piece-wise linear model or a Support-Vector-Regression model.

According to an embodiment of the invention, the regression model 44 is a non-linear model.

However, the regression model may also be linear and may be based, for example, on linear decorrelation techniques, such as Principal Component Analysis.

In step 34, residual mode image data 46 and/or dominant mode image data 48 are determined from the first and second image data 42a, 42b with the aid of the regression model 44.

With the regression model 44, the first and second image data 42a, 42b may be compared and analyzed. In particular, intensities of pixels of the one set of image data 42a may be mapped with the regression model 44 to intensities that are comparable with intensities of corresponding pixels of the other set of image data 42b. In this context, a corresponding pixel may be a pixel at the same position, which may have the same coordinates.

By subtracting the mapped intensities of the one set of image data 42a from the intensities of the other set of image data 42b, a residual mode image (represented by residual mode image data 46) may be computed containing the residuals of the correlation, i.e. the new information added by the second image data 42b, which cannot have been predicted from the first image data 42a with the aid of the regression model 44.

According to an embodiment of the invention, the method comprises the step of: calculating residual mode image data 46 from the first image data 42a and the second image data 42b, such that a pixel of the residual mode image data 46 has an intensity based on the difference of an intensity of the second image data 42b at the pixel and a correlated intensity of the pixel of the first image data 42a, the correlated intensity determinate by applying the regression model to the intensity of pixel of the first image data 42a.

The residual mode image data 42a may be used to visualize which parts of the second image data 42b are truly adding information to the first image data 42a, i.e. are non-redundant and cannot be simply predicted from the first one.

Additionally or alternatively, the parts of the first and second image data 42a, 42b that are predictable from each other may be computed. Again using the regression model 44, a dominant mode image (represented by dominant mode image data 48) may be computed, containing the dominant mode, i.e. the highly correlated component between the two energy images.

According to an embodiment of the invention, the method further comprises the step of: calculating dominant mode image data 48, wherein an intensity of a pixel of the dominant mode image data 48 is based on a correlated component of the pixel of the first image data 42a and second image data 42b with respect to the regression model 44.

Figure 5:
FIG. 5 shows an example of a dominant mode image and a residual mode image generated with a method for processing image data according to an embodiment of the invention.
Figure 6:
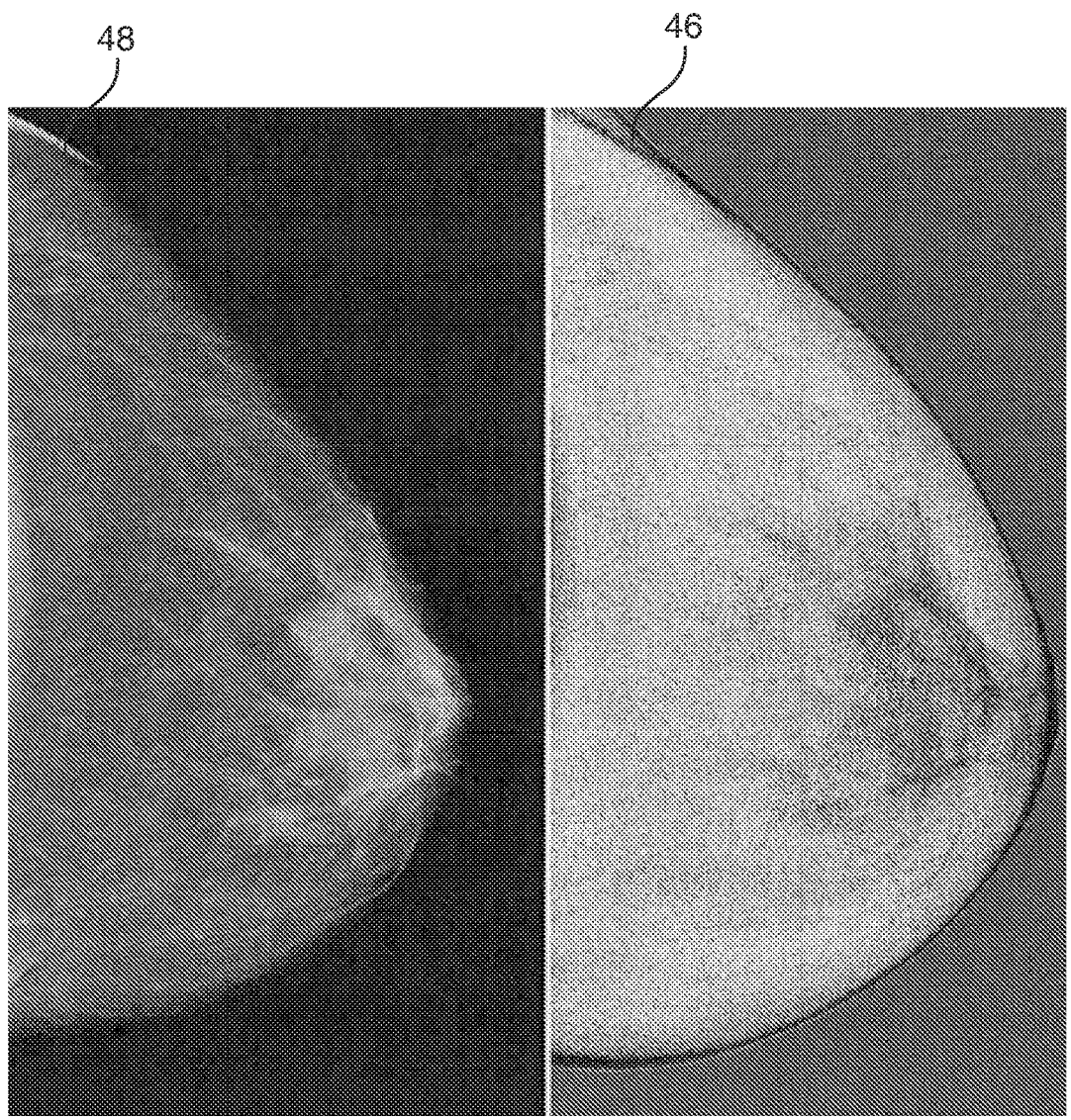
FIG. 6 shows an example of a dominant mode image and a residual mode image generated with a method for processing image data according to an embodiment of the invention.

FIGS. 5 and 6 show examples of dominant mode images 48 and residual mode images 46 that are depicted side by side and that may be displayed in the shown way on a display device 16 as will be explained below.

In step 36, the residual mode image data 46 may further be analyzed to find an intensity threshold above which the intensity difference can be considered meaningful, for example to eliminate noise.

As may be seen from FIG. 6, the residual mode image data 46 may contain mainly noise. An intensity threshold may be set, above which the deviation from the dominant mode image data 48 can be considered meaningful.

The such established threshold intensity of the residual mode image data 46 may be used to display only pixels which are above a specific noise level.

According to an embodiment of the invention, the method further comprises the step of: applying a threshold intensity to the residual mode image data 46, such that pixels of the residual mode image data 46 with an intensity below the threshold intensity are discarded.

For example, the noise level of the residual mode image data 46 may be analyzed by means of a curve of Euler characteristics, i.e. for each possible threshold the number of holes and blobs is counted, to build an Euler histogram. Techniques are known for establishing the Euler characteristic simultaneously for possible thresholds in a single pass over the residual mode image data 46. A threshold intensity may be derived from the curve position at which the Euler characteristics drops below a predefined number, indicating larger spatial structures in the residual mode image data 46.

According to an embodiment of the invention, the threshold intensity is determined such that an Euler characteristic of the residual mode image data 46 drops below a predefined number at the threshold intensity.

In step 38, the residual mode image data 46 and/or the dominant mode image data 48 are displayed on the display device 16.

Figure 3:
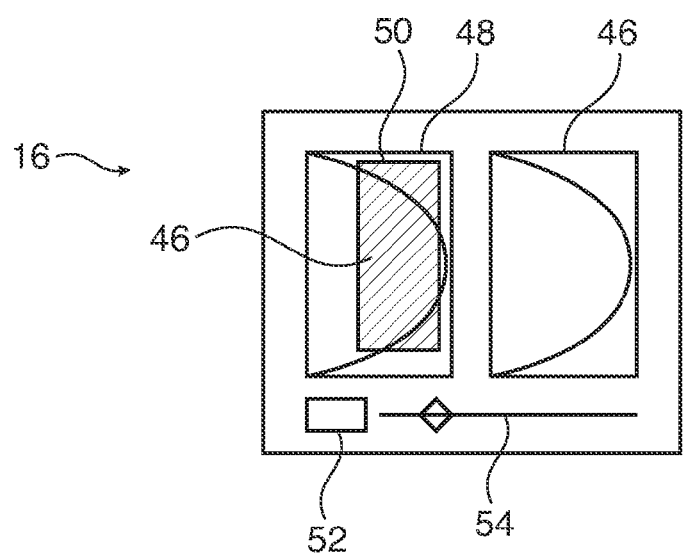
FIG. 3 schematically shows a display device for an X-ray imaging system according to an embodiment of the invention.

FIG. 3 shows an example of a screen content of the display device 16, which may be a CRT or LCD or similar device.

Each set of image data 42a, 42b, 46, 48 may be displayed on the display device. For example, as indicated in FIG. 3, the residual mode image 46 may be presented separately from the dominant mode image 48 as an additional image.

Alternatively or additionally, (at least a part of) the residual mode image 46 may be presented as an overlay or alpha-blended to the dominant mode image 48 (or the other energy images 42a, 42b), either for the whole image area or only for a selected region 50.

It is possible that the residual mode image 46 is presented an overlay to the dominant mode image 48, for example as a color overlay, wherein the opacity is determined by the intensities of the residual mode image 46.

The degree of color overlay may be manually controlled by a user, for example with a slider 54 or with a mouse wheel.

According to an embodiment of the invention, the method further comprises the step of: displaying the residual mode image data 46 together with further image data 42a, 42b, 48 on a display device 16 by overlaying the image data with the further image data 46.

The further image data may be one of the first image data 42a, second image data 42b, and the dominant image data 48.

Furthermore, it is possible that the residual mode image 46 is toggled in place with the further image data 42a, 42b, for example with the aid of a toggle button 52. A user may manually control the toggling of the images.

According to an embodiment of the invention, the method further comprises the step of: displaying the residual mode image data 46 together with further image data 42a, 42b, 48 on a display device 16 by toggling the image data with the residual mode image data 46 by a user command on the display device 16.

As a further possibility, the residual mode image 36 may be gradually alpha-blended in gray-scale and in place with the other image data 42a, 42b, 48. For example, the degree of alpha-blending or the binary toggling may be manually controlled by a user, for example with a slider 54 or mouse wheel.

According to an embodiment of the invention, the method further comprises the step of: displaying the residual mode image data 46 together with further image data 42a, 42b, 48 on a display device 16 by alpha-blending the image data with the residual mode image data 46 by a user command.

On the display device 16, also a region 50 of one of the images 42a, 42b, 46, 48 may be selected by a user. For example, a rectangle may be selected with a mouse.

The selected region 50 may be used for defining a region in the digital image 40 from which the regression model 44 is determined, i.e. the regression model 44 may be determined from the whole image 40 or only from a part of the image 40.

The selected region 50 also may be used for defining a region in one of the images 42a, 42b, 48, to which the residual mode image data 46 is overlaid or alpha-blended.

According to an embodiment of the invention, the residual mode image data 46 is displayed only for pixels of only the selected region 50.

Furthermore, when displayed side by side, two images may be linked such that a mouse click or movement in either one of the two images shows a hair cross at the corresponding position in the other image.

Additionally, the user may freely move with the selected region over the image 42a, 42b, 46, 48 (like a magic magnifier). Thus, the method may be applied to the multiple energy image 40 as a whole, or to a local region of interest, interactively steered by a user like a magic magnifying glass.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for processing a digital image comprising pixels with intensities relating to different energy levels, the method comprising the steps of:
    receiving first image data and second image data of the digital image, the first image data encoding a first energy level and the second image data encoding a second energy level;
    determining a regression model from the first image data and the second image data, the regression model establishing a correlation between intensities of pixels of the first image data with intensities of pixels of the second image data; and
    calculating residual mode image data from the first image data and the second image data, such that a pixel of the residual mode image data has an intensity based on the difference of an intensity of the second image data at the pixel and a correlated intensity of the pixel of the first image data, the correlated intensity being determined by applying the regression model to the intensity of pixel of the first image data.

2. The method of claim 1, wherein the regression model is a non-linear model.

3. The method of claim 1, further comprising the step of:
    selecting a region of the digital image,
    wherein the regression model is determined from pixels of only the selected region and/or the residual mode image data is determined for pixels of only the selected region.

4. The method of claim 1, further comprising the step of:
    calculating dominant mode image data, wherein an intensity of a pixel of the dominant mode image data is based on a correlated intensity of the pixel of the first image data and second image data with respect to the regression model.

5. The method of claim 1, further comprising the step of:
    displaying the residual mode image data together with further image data on a display device by overlaying the image data with the residual mode image data.

6. The method of claim 1, further comprising the step of:
    displaying the residual mode image data together with further image data on a display device by toggling the image data with the residual mode image data on the display device.

7. The method of claim 6, wherein the image data is toggled with the residual mode image data on the display device by a user command.

8. The method of claim 1, further comprising the step of:
    displaying the residual mode image data together with further image data on a display device by alpha-blending the image data with the residual mode image data.

9. The method of claim 1, further comprising the step of:
    applying a threshold intensity to the residual mode image data, such that pixels of the residual mode image data with an intensity below the threshold intensity are discarded.

10. The method of claim 9, wherein the threshold intensity is determined such that an Euler characteristic of the residual mode image data drops below a predefined number at the threshold intensity.

11. The method of claim 1, further comprising the step of:
    recording the first image data and the second image data with an X-ray detector arrangement adapted for acquiring X-rays at different X-ray energy levels.

12. A non-transitory computer-readable medium storing a computer program, executable by a processor, for processing a digital image comprising pixels with intensities relating to different energy levels, the computer-readable medium comprising:
    receiving code for receiving first image data and second image data of the digital image, the first image data encoding a first energy level and the second image data encoding a second energy level;
    determining code for determining a regression model from the first image data and the second image data, the regression model establishing a correlation between intensities of pixels of the first image data with intensities of pixels of the second image data; and
    calculating code for calculating residual mode image data from the first image data and the second image data, such that a pixel of the residual mode image data has an intensity based on a difference between an intensity of the second image data at the pixel and a correlated intensity of the pixel of the first image data, the correlated intensity being determined by applying the regression model to the intensity of pixel of the first image data.

13. A controller for an X-ray imaging system adapted to execute the steps of claim 1.

14. An X-ray imaging system, comprising:
    a detector arrangement for recording first image data with X-rays of a first energy level and for recording second image data with X-rays of a second energy level different from the first energy level;
    a controller for generating residual mode image data from the first image data and the second image data, the controller executing a computer program to perform the steps of:
        determining a regression model from the first image data and the second image data, the regression model establishing a correlation between intensities of pixels of the first image data with intensities of pixels of the second image data; and
        calculating the residual mode image data from the first image data and the second image data, such that a pixel of the residual mode image data has an intensity based on a difference of an intensity of the second image data at the pixel and a correlated intensity of the pixel of the first image data, the correlated intensity being determined by applying the regression model to the intensity of pixel of the first image data; and
    a display device for displaying the residual mode image data.

* * * * *